(12) United States Patent
Gross et al.

(10) Patent No.: US 6,346,095 B1
(45) Date of Patent: Feb. 12, 2002

(54) NEEDLE AND METHOD FOR DELIVERY OF FLUIDS

(75) Inventors: Joseph Gross, Moshav Mazor; Haim Danon, Kiryat Ona, both of (IL)

(73) Assignee: Elan Corporation, plc (IE)

( * ) Notice: Subject to any disclaimer, the term of this patent is extended or adjusted under 35 U.S.C. 154(b) by 0 days.

(21) Appl. No.: 09/778,332

(22) Filed: Feb. 6, 2001

Related U.S. Application Data

(63) Continuation of application No. 09/202,176, filed as application No. PCT/IE97/00041 on Jun. 4, 1997, now Pat. No. 6,261,272.
(60) Provisional application No. 60/019,714, filed on Jun. 13, 1996.

(30) Foreign Application Priority Data

Jun. 10, 1996 (IE) .................................. 960427

(51) Int. Cl.⁷ ............................................. A61M 5/32
(52) U.S. Cl. ....................................................... 604/272
(58) Field of Search ................................ 604/272, 274, 604/264, 131, 132, 523

(56) References Cited

U.S. PATENT DOCUMENTS

| 1,740,174 A | 12/1929 | Hevern |
| 2,653,607 A | 9/1953 | Deans |
| 2,748,769 A | 6/1956 | Huber |
| 3,076,457 A | 2/1963 | Copen |
| 4,402,308 A | 9/1983 | Scott |
| 4,413,993 A | 11/1983 | Guttman |
| 4,537,593 A | 8/1985 | Alchas |
| 4,781,688 A | 11/1988 | Thoma et al. |
| 4,784,638 A | 11/1988 | Ghajar et al. |
| 4,790,830 A | 12/1988 | Hamacher |
| 4,838,877 A | 6/1989 | Massau |
| 4,886,499 A | 12/1989 | Cirelli et al. |
| 5,449,351 A | 9/1995 | Zohmann |
| 5,643,228 A | 7/1997 | Schucart et al. |

FOREIGN PATENT DOCUMENTS

| EP | 0619983 A2 | 10/1994 |
| PL | 51532 | 7/1966 |

*Primary Examiner*—Manuel Mendez
(74) *Attorney, Agent, or Firm*—Caesar, Rivise, Bernstein, Cohen & Pokotilow, Ltd.

(57) ABSTRACT

A needle (10) for the delivery of a liquid to a subject comprises a shaft (11) having an internal surface defining a longitudinally extending internal bore open at one end (15) to receive a liquid supply, the other end (16) being sharpened for penetration of the skin of the subject. A plurality of apertures (18) are provided, each in the form of a cut extending across the external surface of the side of the shaft (11) at a sufficient depth to establish communication with the bore. The external aperture area is approximately three times greater than the internal aperture area, thereby ensuring that the liquid is delivered to a large surface area of tissue to improve absorption and eliminate fluctuations in the delivery rate. The needle (10) can be mass-produced by aligning a batch of shafts alongside one another and running a grinder across the surfaces of the shafts to create the apertures (18) in the entire batch of needles simultaneously.

26 Claims, 7 Drawing Sheets

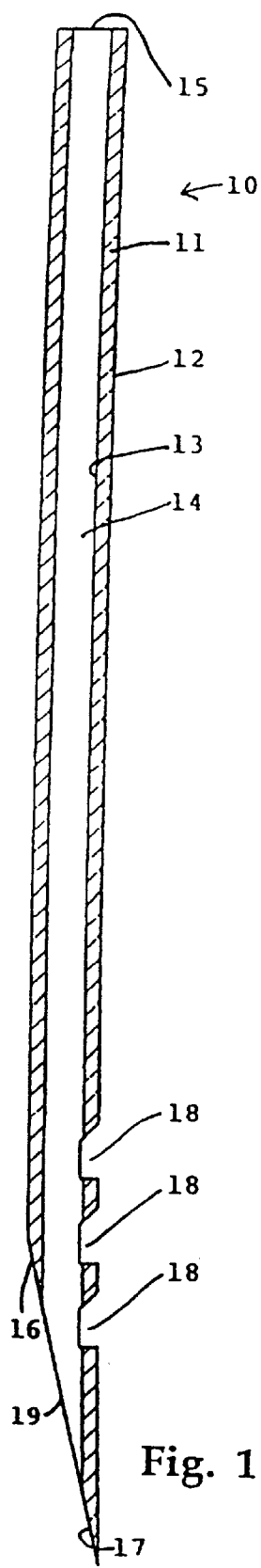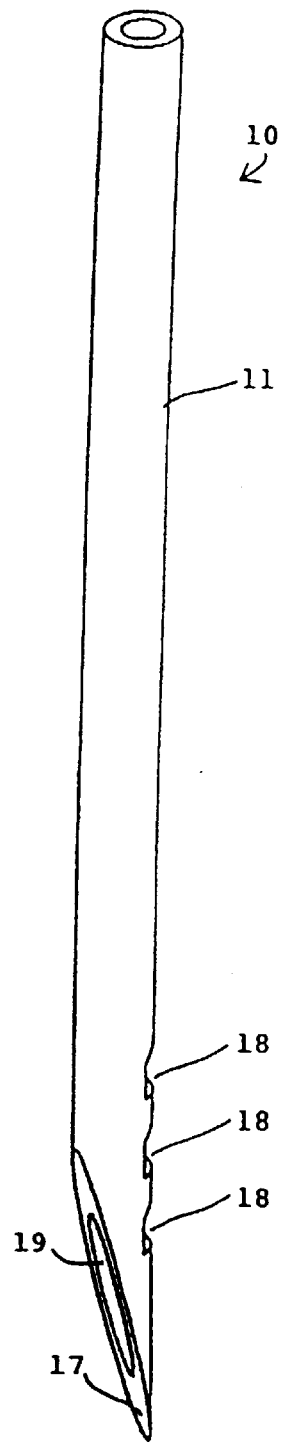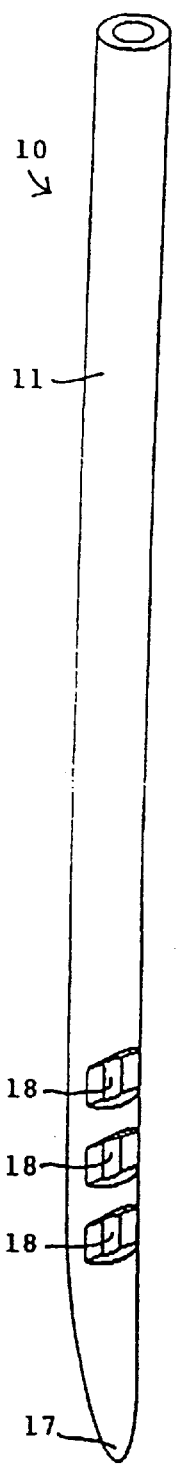
Fig. 1
Fig. 2
Fig. 3

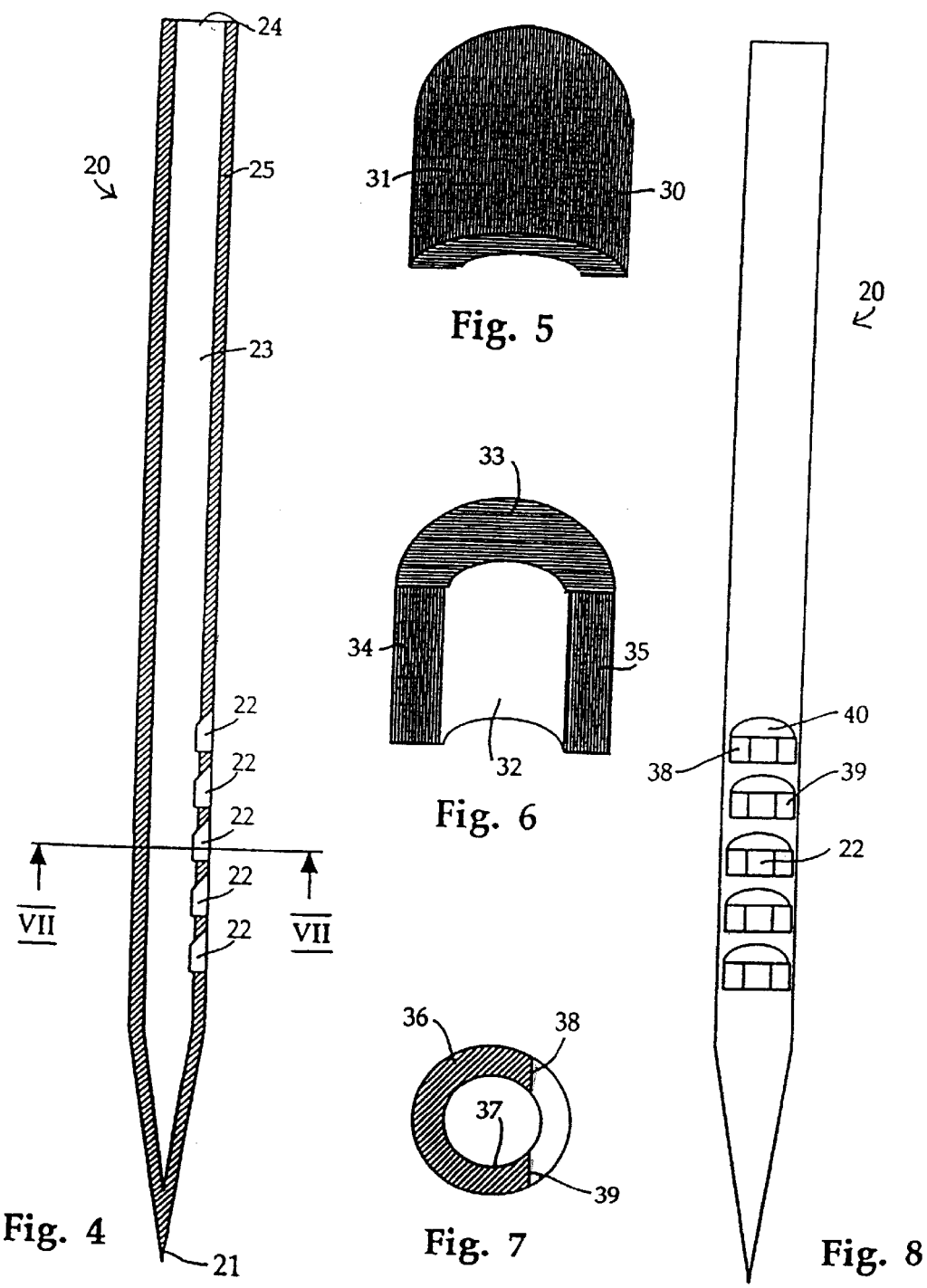

NEEDLE AND METHOD FOR DELIVERY OF FLUIDS

RELATED APPLICATION

This application is a continuation of U.S. patent application Ser. No. 09/202,176, now U.S. Pat. No. 6261272 filed on Jun. 1, 1999, entitled NEEDLE FOR SUBCUTANEOUS FLUID DELIVERY, which is a 371 PCT/IE97/00041 filed on Jun. 4, 1997, and claims the benefit of provisional application 60/019,714, filed Jun. 13, 1996, which is assigned to the same assignee as this invention and whose entire disclosure is incorporated by reference herein.

TECHNICAL FIELD

This invention relates to needles for the delivery of liquids to human or animal subjects.

BACKGROUND ART

The standard needle used for subcutaneous or intramuscular injections is in the form of a hollow shaft provided with a sharpened open end. This type of needle has been found to be unreliable in ensuring accurate delivery rates, in particular when used in conjunction with an infusion pump or some other delivery device which depends for delivery on the magnitude of pressure applied to the liquid being delivered.

The lack of accuracy is thought to be due to the build up of pressure at the delivery point which opposes the driving pressure applied to the liquid.

Others have tried to combat the problem by designing needles which were intended to avoid the problem of pressure build up arising from the orifice becoming plugged by tissue on entry into the skin.

U.S. Pat. Ser. No. 4,413,993 (Guttman), U.S. Pat. Ser. No. 4,790,830 (Hamacher), and U.S. Pat. Ser. No. 4,838,877 (Massau) each disclose a hypodermic or intravenous delivery needle having one or more apertures located on the side of the shaft removed from the sharpened tip.

U.S. Pat. Ser. No. 2,748,769 (Huber) discloses a hypodermic needle having a curved or bent tip cut in a plane that extends along the side of the needle towards which the bend is made and thereby providing an orifice which is not plugged by tissue upon insertion into a subject, the curved surface being provided with an auxiliary delivery orifice which ensures delivery when the main orifice rests against a vein wall.

U.S. Pat. Ser. No. 3,076,457 (Copen) discloses a hypodermic needle having an aperture at the tip and also having an opening which extends along the side of the shaft for part of its length.

None of these needles provides a satisfactory solution to the problem of ensuring accurate delivery using a delivery device in which the delivery rate depends on the generation of pressure, because in each case, the problem which has been addressed has been the provision of an additional orifice which will not become plugged upon insertion or which will not rest against a vein wall. While these problems must be addressed in designing a needle for use with an automated drug delivery device, it has been found that these factors alone do not account for the major variations in delivery rate which occur when using a device which depends for delivery on pressurising a supply of drug.

It has been found, when conducting tests of devices which operate on the pressurised reservoir principle, that there are large variations in the resistance to delivery into the skin not only when comparing different subjects or different delivery sites on the same subject (which could be accounted for by differences in tissue composition at the delivery site), but also when the resistance to delivery is monitored over time during a single test at a single site.

If the resistance to delivery (i.e. the impedance to the flow of drug) varies while the pressure effecting delivery remains fixed, then clearly the delivery rate (which is dependent on the difference in pressure between the reservoir and the delivery site) will fluctuate. Clearly this has serious implications for the delivery accuracy of such devices.

The best results in subcutaneous delivery tests of this type are obtained when using a needle such as that disclosed by Huber or by Copen (see above), wherein the aperture has a greater external surface area than internal surface area. Without wishing to be bound by any theoretical explanation, it is conjectured that the major obstacle to ensuring accurate delivery rates is not that the orifice becomes plugged, but rather that the difficulty arises from poor absorption by the tissue adjacent to the orifice(s), and/or from variations in the structure of the tissue at the orifice. This means that the drug accumulates at the orifice and the pressure builds up until absorption commences, since a given surface area of tissue can only absorb a certain amount of drug at a given pressure. In cases where the external aperture surface area is increased relative to the internal aperture surface area, the absorption (by a larger tissue area) is correspondingly better and fluctuations are reduced.

Nevertheless, it is not practicable to replace conventional delivery needles with needles of the type disclosed by Huber or Copen because of the substantial difference in manufacturing cost involved. A conventional delivery needle can be formed by cutting hollow steel tubing to the correct length, and grinding or in some other way machining the cut end to provide the necessary sharpness for skin penetration. The thus formed tip is of course automatically provided with a delivery orifice, and the needle is inexpensive.

In order to manufacture a needle of the type disclosed in any of the prior art documents referred to above, the initial steps of creating a needle must first be followed, and then the additional holes or orifices must be machined into the side of the needle. In the case of small diameter needles such as needles having an external diameter of less than 0.7 mm and an internal diameter of less than 0.45 mm (approximately 22 gauge or higher), this is a relatively complicated task when compared to the preceding steps.

The orifice may have to be created by laser drilling a hole at the correct point, by pressing a revolving disc cutter against the curved surface of the Huber needle, or by removing a quarter-cylinder length from the side of the shaft in the case of the Copen needle (no indication is given by Copen as to how one would go about creating the type of aperture disclosed). In all cases, the operations require careful positioning of the needle relative to the machining means, and a delicate machining of each and every needle. The magnitude of the cost differential between such needles and conventional needles arises from the differences between the complexity of the manufacturing processes involved in each type of needle.

It is an object of the present invention to provide a needle which has improved delivery characteristics when connected to an infusion system, and which can be manufactured cheaply and easily in large numbers at the same time unlike the prior art needles referred to above.

DISCLOSURE OF INVENTION

Accordingly, the invention provides a needle for the delivery of a liquid to a subject, comprising a shaft having an internal surface defining a longitudinally extending internal bore open at one end thereof to receive a liquid supply, the other end of the shaft being sharpened for penetration of the skin of the subject, the shaft being provided with at least one aperture in the form of a cut extending across the external surface of the side of the shaft at a sufficient depth to establish communication with the bore, wherein the external aperture area is greater than the internal aperture area, said areas being defined by the surface areas of the material removed between the external and internal surfaces of the shaft, respectively.

Because the or each aperture is in the form of a cut extending across the shaft, rather than a section removed along the length of the shaft or a hole drilled into or through the shaft (as in the prior art), the needle according to the present invention is far easier to manufacture. It is as easy to manufacture a large number of identical needles (by extending a cut across a plurality of shafts at the same time) as to form a cut in a single needle.

Additionally, the or each aperture thus formed has a larger external surface area than internal surface area, so that the needle delivers drug to a large area of tissue, thereby increasing the capability of absorption. The improved delivery characteristics of the needle will be illustrated below. In all needles where a hole is drilled into the surface of the needle, the external surface area (as defined above) is in fact less than the internal surface area due to the greater curvature of the internal surface.

Suitably, the sharpened end of the needle is in the form of a bevelled or conical tip and the aperture is formed by a linear cut made at an angle to the internal bore which is greater than or equal to the angle between the bevelled or conical surface and the longitudinal bore.

In a presently preferred embodiment, the cut extends in a direction approximately perpendicular to the longitudinal bore.

This allows the aperture(s) to be formed at exactly the same distance from the needle tip in a batch of needles by aligning the ends of a row of parallel adjacent needles and machining a groove or cut across the surface of the row, to form a series of identical apertures in the aligned needles.

Suitably, the width of the cut on the external surface of the shaft is greater than the width of the cut on the internal surface of the shaft. Preferably, the width of the cut on the external surface of the shaft is at least twice the width of the cut on the internal surface of the shaft.

It is preferred to maximise the external width of the cut relative to the internal width of the cut, so as to maximise the ratio between external and internal aperture areas.

According to a preferred embodiment, the shaft has a C-shaped cross section at the locus of the aperture, defined by the partial circumferences of the internal and external shaft surfaces and by the aperture surfaces formed by the cut which connect the internal and external shaft surfaces, said aperture surfaces being co-planar.

Such a cross-section can be obtained by manufacturing the needles as described in detail below.

Preferably, the shaft is provided with a plurality of said apertures, each of which is located a different distance from the sharpened end of the needle.

The provision of a plurality of apertures increases the area of tissue to which the needle can deliver. Additionally, the apertures can be spaced along the length of the shaft to provide more delivery sites. If a single aperture is provided on a needle, all of the tissue at the aperture may have poor absorption. By increasing the number of apertures, the probability that at least one aperture will deliver to a site with improved absorption is maximised.

Preferably, the ratio between the external aperture area and the internal aperture area is greater than or equal to the ratio between the external width of the shaft and the internal width of the bore. In general, this provides a substantially larger external aperture surface area.

Preferably, the depth of the cut relative to the external surface varies along the length of the cut. Further, preferably, the depth of the cut increases from zero at either end of the cut to a maximum depth towards the centre of the cut which is greater than or equal to the thickness of the wall of the shaft at that point.

In a preferred embodiment, the variation in the depth of the cut results from a planar cut surface machined across a curved external surface. Nevertheless, it is also possible to provide a curved machined cut across the external surface.

Suitably, the sharpened end is provided with a terminal orifice to assist in delivery of the liquid through the needle.

Preferably, the or each aperture is formed by the operation of a grinder on the surface of the shaft. Alternatively, the or each aperture is formed by another machining operation such as milling (although grinding is at present preferred due to lower costs and the fact that it is not as likely to give rise to difficulties such as chips being produced by the operation.

Preferably, the external and internal surfaces of the needle are defined generally in cross-section by two concentric circles. There is no strict necessity to use a circular needle with a circular bore, however, other than the fact that the tubing for such a needle is readily and cheaply available.

The invention also provides a method of manufacturing a plurality of delivery needles, comprising the steps of arranging a plurality of tubular shafts having internal bores in a row in parallel with one another and performing a machining operation across the row of shafts to create at least one aperture in the external surface of the side of each shaft at a sufficient depth to establish communication with the bore of each shaft.

It will be appreciated that this operation can be carried out on scores or hundreds of needles simultaneously. The manufacture of a batch of 200 needles according to the invention can be completed in only a few seconds. To carry out the manufacture of 200 of the prior art needles referred to above, on the other hand, would take 200 times the length of time required to carry out the machining operation for one needle, which does not include the additional time involved in positioning each successive needle in the correct position for machining.

Preferably, the machining operation includes running a grinder across the row of shafts to grind a line of grooves across the surfaces of the shafts, the grooves being sufficiently deep to provide communication between the external surfaces of the shafts and the internal bores of the shafts.

Optionally, the process also comprises the step of sharpening the shafts while they are arranged in a row.

In addition, the invention provides a liquid delivery device for delivering a liquid to a subject, comprising a reservoir for the liquid, means for driving the liquid from the reservoir to an outlet, and a delivery needle according to the invention in communication with the outlet.

Suitably, in such a device, the reservoir and driving means are located in a housing which is provided with means for attachment to the skin of the subject and wherein the delivery needle protrudes from the housing in use such that it penetrates the skin of the subject upon application of the device to allow delivery of the liquid through said needle.

Preferably, the delivery rate of the device is calibrated according to the pressure exerted by the driving means. By incorporating the needle according to the invention, such a device is freed from the variations and fluctuations in delivery rate which have otherwise been found to exist.

The invention will be further illustrated by the following description of embodiments thereof, given by way of example only with reference to the accompanying drawings.

BRIEF DESCRIPTION OF DRAWINGS

FIG. 1 is a sectional elevation of a first embodiment of a needle according to the invention;

FIG. 2 is a first perspective view of the needle of FIG. 1;

FIG. 3 is a second perspective view of the needle of FIG. 1;

FIG. 4 is a sectional elevation of a second embodiment of a needle according to the invention;

FIG. 5 is a first perspective view of the material removed to create the apertures in the needle of FIG. 4;

FIG. 6 is a second perspective view of the material removed to create the apertures in the needle of FIG. 4;

FIG. 7 is a cross-sectional elevation of the needle of FIG. 4 at the locus of one of the apertures taken along the line VII–VII in FIG. 4;

FIG. 8 is a front elevation of the needle of FIG. 4;

MODES FOR CARRYING OUT THE INVENTION

Figures 9, 10:
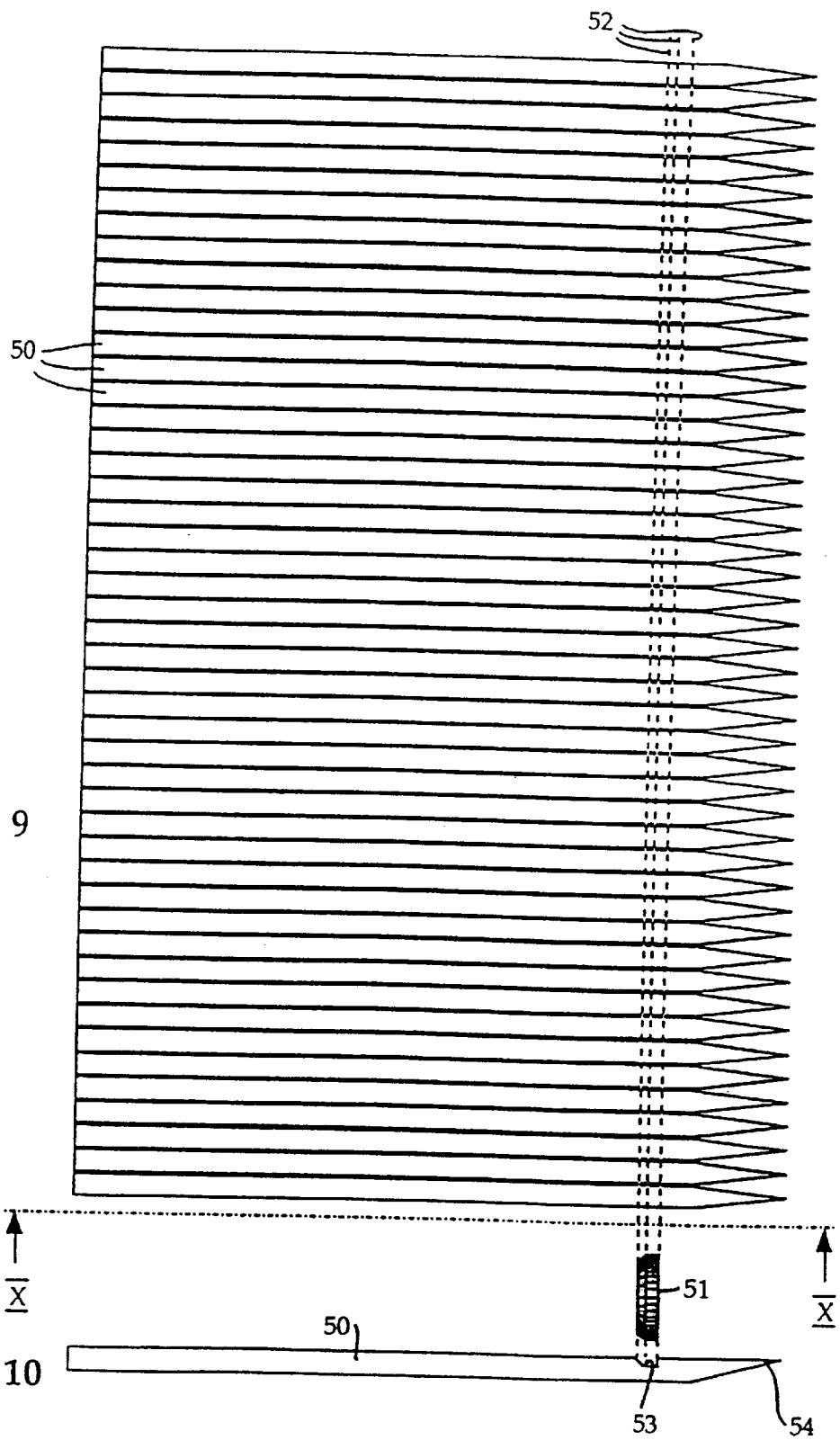
FIG. 9 is a plan view of a batch of needles during a step in the manufacturing process.
FIG. 10 is a side elevation of one of the needles shown in FIG. 9.

In FIG. 1 there is indicated, generally at 10, a needle according to the invention. The needle 10 comprises a shaft 11 having an external surface 12 and an internal surface 13 which defines a longitudinally extending internal bore 14.

The bore 14 is open at one end 15 to receive a supply of drug for delivery (for example by connection to a drug pump or a syringe) and the other end 16 of the needle is also open and is sharpened with a bevelled tip 17 to penetrate the skin of a subject.

The shaft 11 is provided with three identical apertures 18 spaced at intervals from the tip 17. The apertures 18 permit communication between the internal bore 14 and the exterior of the needle 10. Communication between the bore 14 and the exterior of the needle 10 is also facilitated by a terminal orifice 19 at end 16 of the shaft.

Referring additionally to FIGS. 2 and 3, the needle 10 can be seen in perspective views which show shaft 11, tip 17, apertures 18 and orifice 19. FIG. 3 illustrates the particular shape of the apertures 18, each of which can be seen to be in the form of a cut which extends across the shaft 11. The external surface area of each aperture is approximately three times that of the internal surface area of each aperture, thereby increasing the area of tissue which is presented to each aperture upon penetration into the skin of a subject.

Similar apertures can also be seen in FIG. 4, in which a second embodiment of needle according to the invention, indicated generally at 20, is shown. Needle 20 is identical to needle 10 (FIGS. 1–3) apart from the shape of the sharpened end 21 and from the fact that the side of the needle is provided with five rather than three apertures 22.

In needle 20, the sharpened end 21 is closed, i.e. the internal bore 23 is only open at the top 24 of the needle 20 and at the apertures 22. The number of apertures can be chosen to suit the delivery rate which is required and the site into which the shaft 25 is to be inserted. A needle inserted into an area of tissue which is rich in capillaries or into a vein will not require as many apertures as a needle inserted into a site which is deficient in blood vessels or a site at which the number of blood vessels varies over small distances.

FIG. 5 illustrates the shape of the apertures 18,22 in the needles 10,20 of FIGS. 1–3 and 4 by showing the shape of the material 30 which is removed to give rise to the apertures 18,22. FIG. 6 shows the material 30 from the opposite direction from which it is viewed in FIG. 5. In comparing the two views it can be seen that the surface area 31 (FIG. 5) of material removed from the exterior surface 12 (see FIG. 1) of the needle is considerably larger than the surface area 32 (FIG. 6) of material 30 removed from the internal surface 13 (FIG. 1). This relates directly to the area of tissue which is presented to the apertures 18, 22 for absorption of the liquid delivered in use.

Referring to FIG. 6, the end surface 33 of the material 30 is in a plane which makes an angle of 45° with the plane of the cut surfaces 34,35 which bridge what were originally the interior and exterior surfaces of the shaft. This angled surface assists in the insertion of the needle into the skin of the subject, and it also serves to further increase the external aperture surface area.

In FIG. 7, the shaft 25 of the needle 20 of FIG. 4 is viewed in cross-section at the locus of one of the apertures 22. It can be seen from this view that the shaft has a C-shaped cross-section at this point defined by the partial external circumference 36 of the shaft 25 at this point, the partial internal circumference 37 of the shaft 25 at this point, and the co-planar cut surfaces 38, 39 which are complementary to the cut surfaces 34,35 visible in FIG. 6.

For the purposes of clarity, FIG. 8 shows needle 20 in a front elevation, from which the large external surface area of the each aperture 22 is clearly visible. The aperture area is increased by virtue of surface 40 (which is complementary to surface 33 in FIG. 6) being angled at 45° to the plane of the cut surfaces 38, 39.

The method of manufacture of needles according to the invention can be understood with reference to FIG. 9, which shows a plurality of identical needles 50 aligned adjacent and parallel to one another. The needles are clamped into this position and the apertures in the sides of the needles are formed by machining a cut across the row of needles using a cutting tool such as a grinder 51. Dotted lines 52 illustrate the path of the grinder, and referring additionally to FIG. 10, the shape of the aperture 53 formed in a needle 50 can be equated with the path of the grinder 51. The bevelled tips 54 of the needles can be cut either before or after the apertures are cut, or the tips can be cut at the same time as the apertures, taking advantage of the fact that the needles are already aligned and clamped into position.

Figures 11, 12:
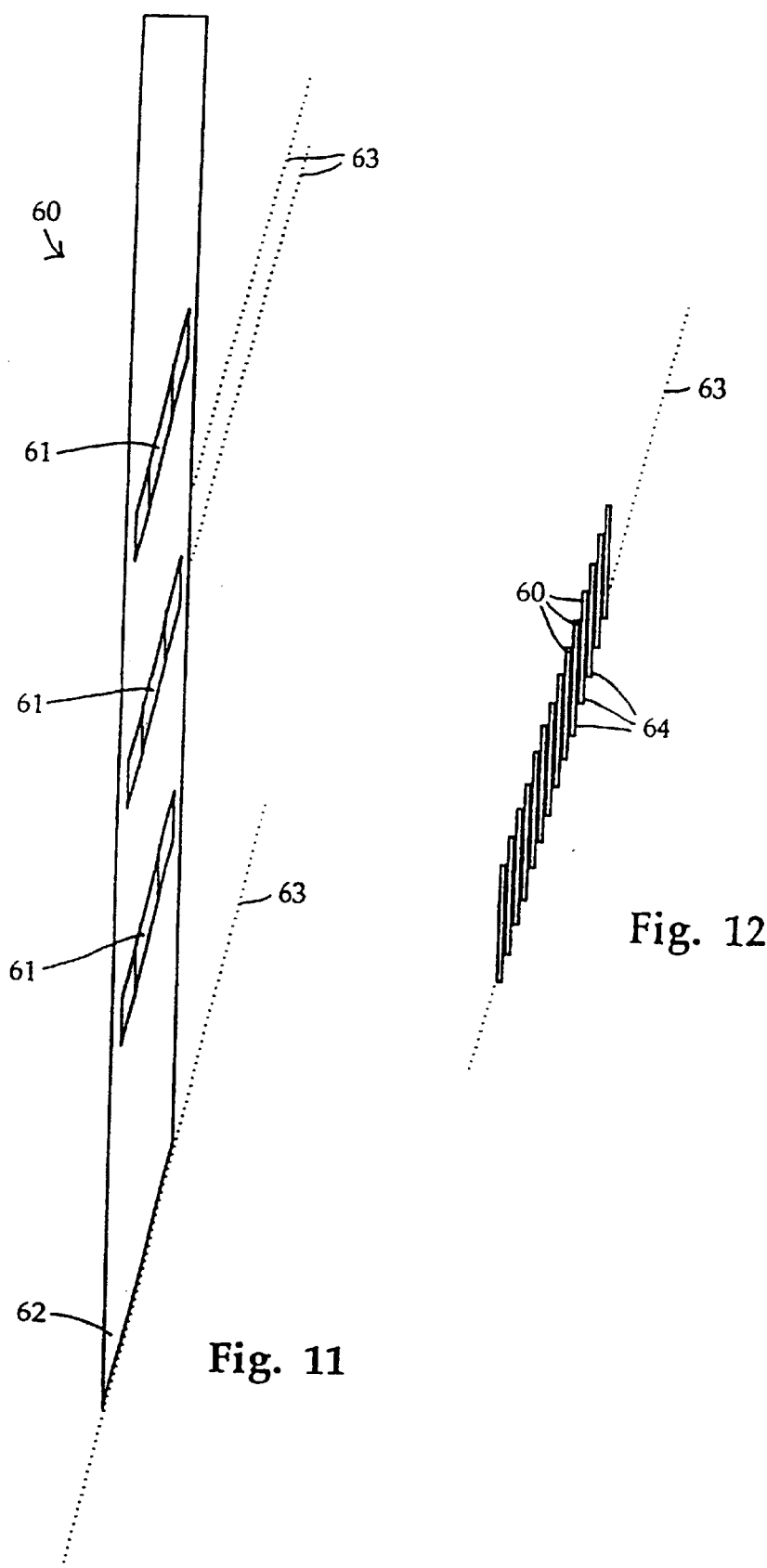
FIG. 11 is a front elevation of a third embodiment of a needle according to the invention.
FIG. 12 is a plan view of a batch of needles similar to the needle of FIG. 11, shown during a step in the manufacturing process.

In FIG. 11, there is indicated, generally at 60, a third embodiment of needle according to the invention. In this embodiment, apertures 61 are formed by machining a row of cuts across the needle at an angle equal to the bevelled angle of the tip 62. Dotted lines 63 indicate the parallel paths of the cutter which creates the bevelled tip 62 and the apertures 61.

Referring additionally to FIG. 12, it can be seen that a plurality of needles 60 can be aligned adjacent to and parallel with one another but laterally displaced, and the ends 64 of the needles 60 can be bevelled by cutting the needles along this row (the path of the cutter again being indicated by dotted line 63. The apertures 61 (FIG. 11) can then be cut along a parallel path while the needles 60 are aligned as shown.

Figure 13:
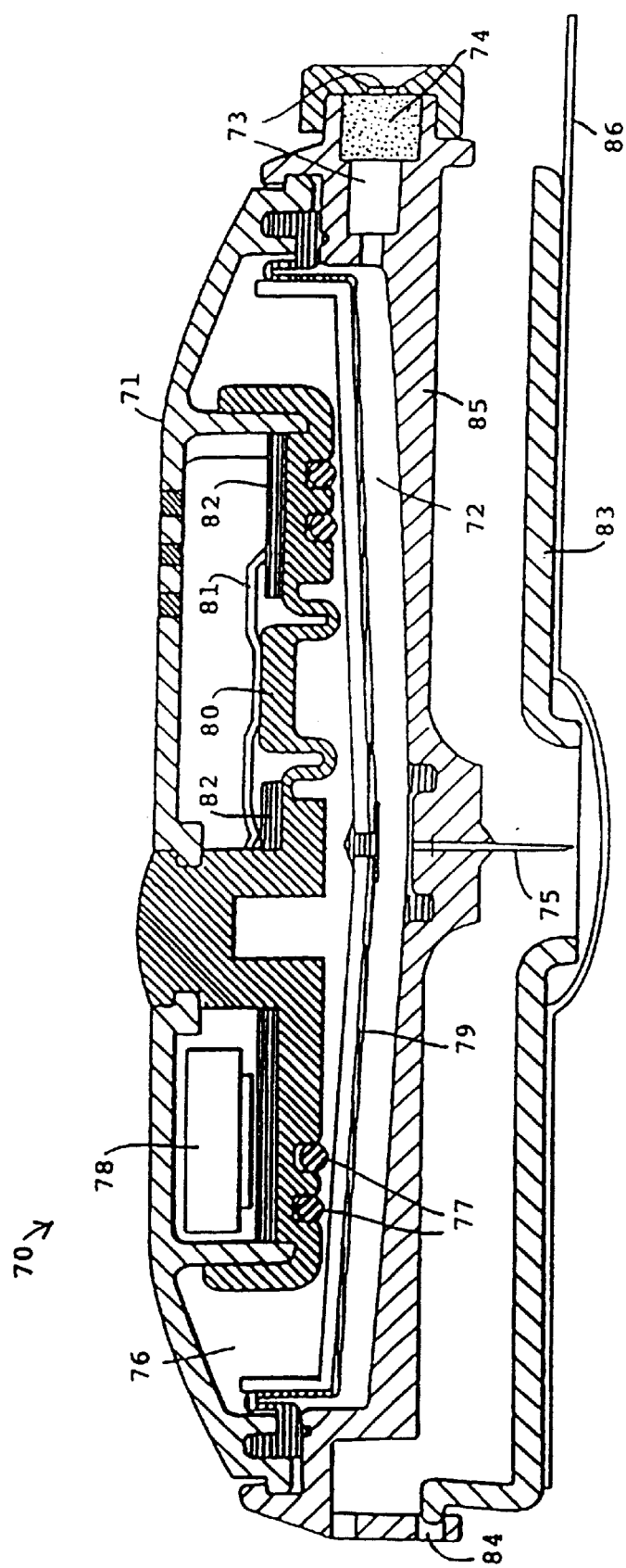
FIG. 13 is a sectional elevation of a drug delivery device according to the invention.

In FIG. 13, there is indicated, generally at 70, a liquid delivery device according to the invention, which is suitable for use as an automated drug delivery device. The device 70 comprises a housing 71 containing a reservoir 72 which is filled with a drug by injection into a filling port 73 sealed with a self-sealing plug 74. Reservoir 72 communicates with a delivery needle 75 identical to the needle 10 illustrated in FIG. 1.

The housing 71 also houses a gas generation chamber 76 containing an electrolyte which generates a gas when a pair of electrodes 77 is energised by power supplied by a battery 78. Chamber 76 is separated from reservoir 72 by a displaceable membrane 79 such that when the electrodes 77 are energised to generate a gas, the chamber 76 expands and thereby forces membrane 79 downwards to expel the liquid contained in reservoir 72 out of needle 75. Upon termination of delivery (when the reservoir 72 has emptied) or in the event of a blockage, a diaphragm 80 is forced upwards by the increased pressure in chamber 76 to lift a conductive element 81 bridging a pair of contacts 82, thereby breaking the circuit which is used to energise the electrodes.

The housing 71 is provided with a displaceable cover 83 provided with a snap mechanism 84 which allows it to snap between a first position as shown (wherein the needle 75 is concealed) and a second position wherein the cover 83 lies against the lower surface 85 of the housing 71. Two additional snap mechanisms (not shown) are located at 120° intervals around the periphery of the (circular) housing 71 and cover 83. The cover 83 is provided with a release liner 86 which is removed before use to reveal an adhesive surface on the bottom of the cover 83.

In use, the release liner 86 is removed and the cover 83 is placed against the skin of the subject (to which it adheres), and the housing 71 is then pressed against the skin causing the cover 83 to snap towards the housing and thereby projecting the needle 75 into the skin of the subject. Needle 75 projects into the skin by 5 mm in this embodiment, and the apertures 18 lie approximately 2.5–4.5 mm below the surface of the skin. The battery 78 is energised by a start button (not shown) and delivery commences as a result of the generation of gas.

Because the subcutaneous (resistive) pressure, i.e. the impedance to flow of the drug, is reduced as a result of the needle design, the liquid can be pumped into the skin at a constant rate, with less expenditure of energy than when a conventional needle is used. The device shown is a relatively simple embodiment, and it will be appreciated that the invention is in no way limited to this device; in particular, more sophisticated devices in which the delivery rate can be varied would benefit from the incorporation of a needle according to the invention. Alternatively, the device could utilise a driving means other than the generation of gas by an electrolytic cell, and the skilled person will be aware of a wide range of automated drug delivery devices in which the delivery rate is dependent at least in part on the pressure opposing delivery through a prior art needle.

Figure 14:
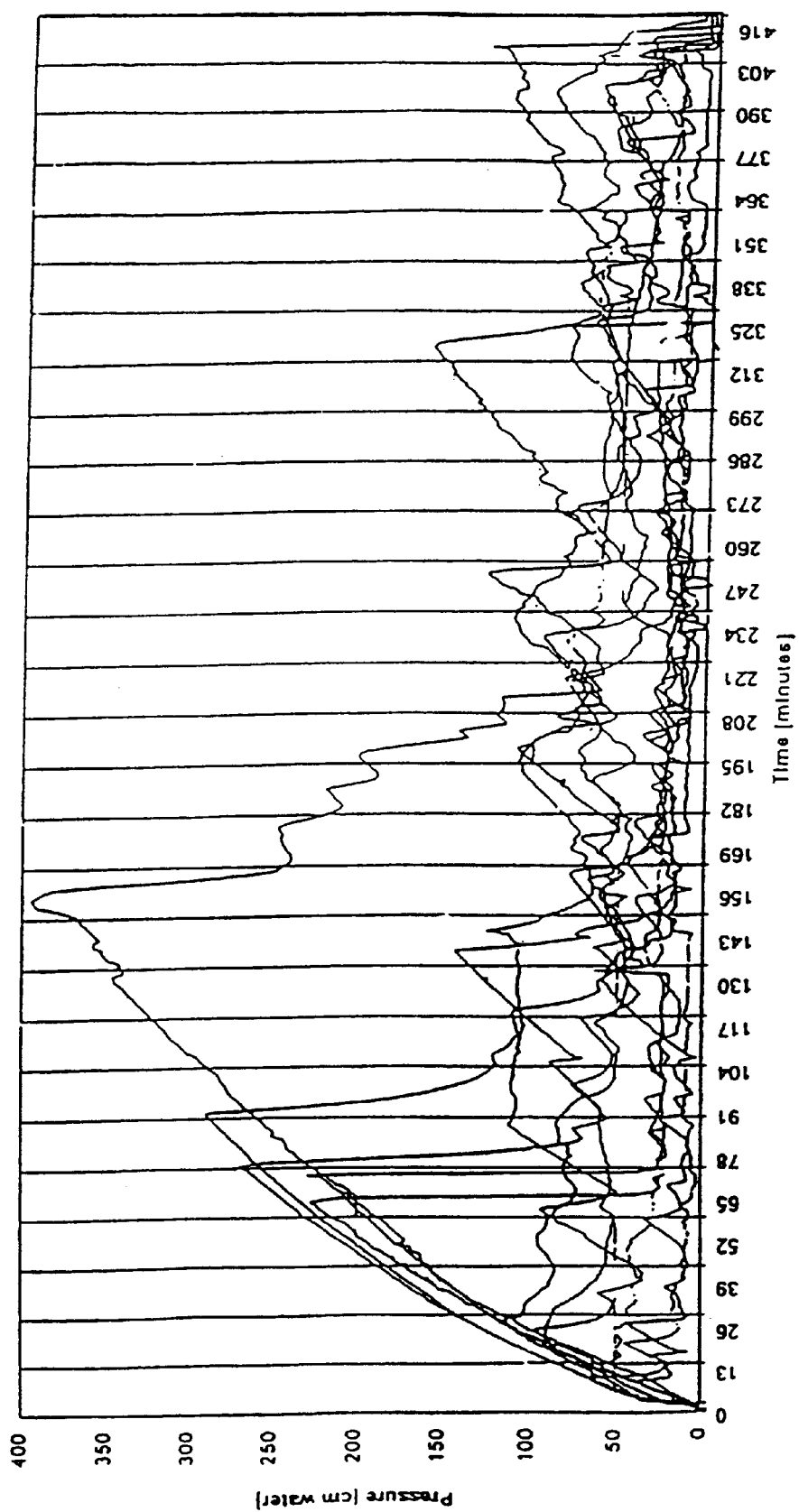
FIG. 14 is a graph illustrating the variation in pressure opposing delivery during a test of a known drug delivery device.

In FIG. 14, there is plotted a series of measurements of pressure opposing delivery from a device according to the invention operating on the same delivery principle as the device of FIG. 13, but in which a conventional bevelled delivery needle was used. The pressure measurements are plotted in centimeters of water (10 cm $H_2O$=981 Pa), and the measurements were carried out over a period of approximately seven hours using a pressure transducer which transmitted the measured subcutaneous pressures to a data logging apparatus. A series of 15 tests was carried out using a standard delivery needle with six different volunteers, and it can be seen that the pressure measurements fluctuated considerably. The standard pattern followed is a steady build-up of pressure followed by a sudden release, and this occurs to a greater or lesser extent in the various tests. What this means in terms of drug delivery, therefore, is that although the device is attempting to pump drug at a constant rate, the subject receives a series of bursts of drug.

Figure 15:
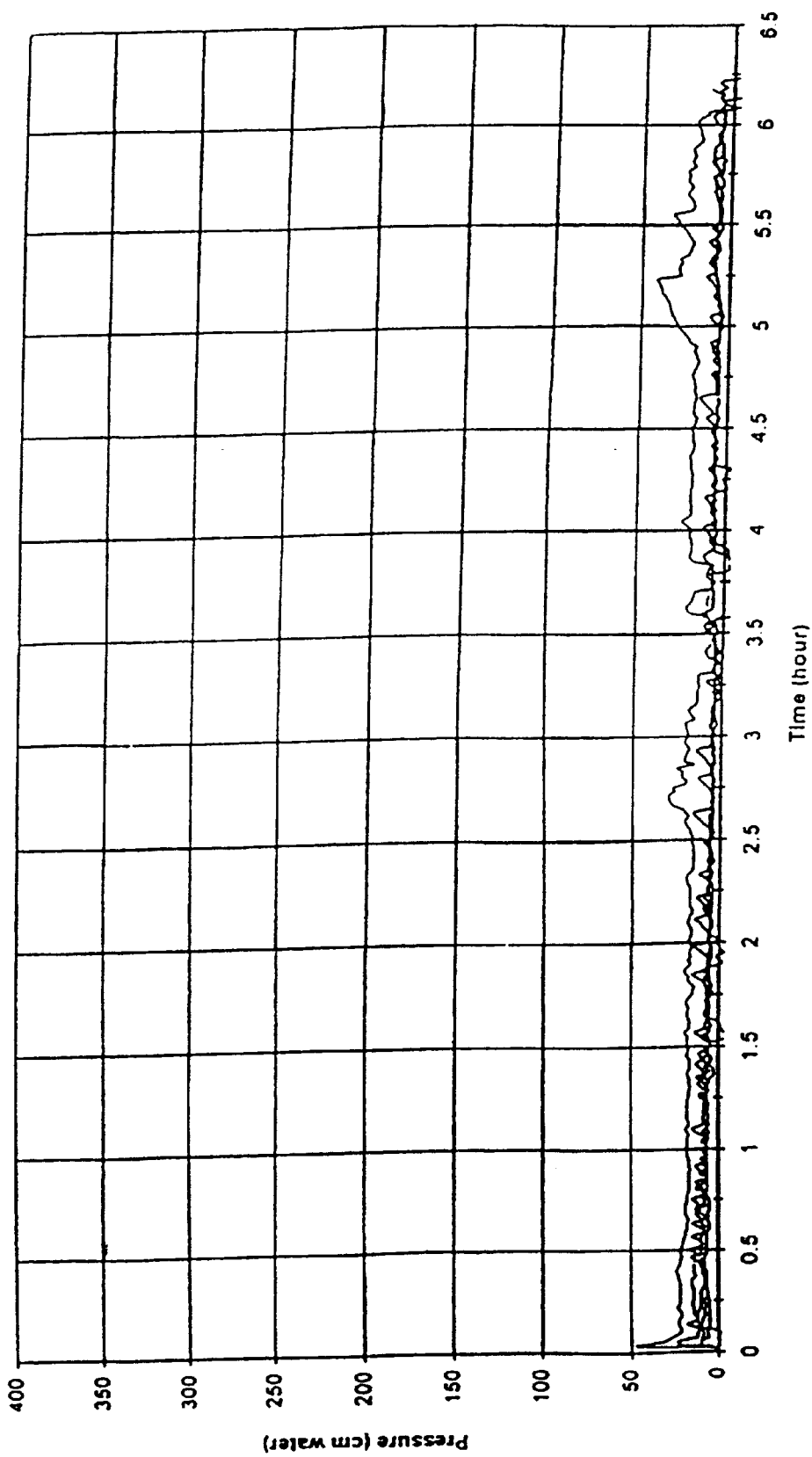
FIG. 15 is a graph illustrating the variation in pressure opposing delivery during a test of a drug delivery device according to the invention.

In FIG. 15, one can see the results obtained when the same test was repeated, except that a device according to the invention was used (i.e. having a needle as illustrated in FIG. 1). The fluctuations were practically eliminated indicating that the needle caused the liquid to be absorbed constantly without building up at the delivery site. Whereas the peak pressures experienced in the tests illustrated in FIG. 14 were in many cases between 200 and 400 cm $H_2O$ (approximately 20–40 kPa or 0.2–0.4 atm), the tests in FIG. 15 show that in all cases the pressure remained below 50 cm $H_2O$ (approximately 5 kPa or 0.05 atm) and generally was less than 25 cm $H_2O$ (approximately 2.5 kPa or 0.025 atm). In each case, the tests were carried out on healthy adult volunteers under controlled clinical trial conditions to ensure comparability and reliability of results for evaluation of the invention.

We claim:

1. A method for the delivery of a liquid into or through the skin of a subject, comprising:

(A) providing a needle comprising a tubular sidewall and a sharpened end for penetrating the skin of the subject, said tubular sidewall having a longitudinal axis, a bore extending along said longitudinal axis, an exterior surface and at least one aperture in the form of a cut in said sidewall extending transversely to said longitudinal axis and in communication with said bore, said aperture having an inlet at said bore and an outlet at said exterior surface, said outlet being substantially larger than said inlet and shaped to be resistant to clogging;

(B) causing said needle to penetrate at least into the skin of the subject; and (C) introducing the liquid into said bore and out through said at least one aperture, whereupon the liquid passes through said at least one aperture and out of said outlet for absorption into an area in the skin or beneath the skin contiguous said at least one aperture to facilitate the transfer of the liquid to the area.

2. The method of claim 1 wherein the liquid is delivered at a rate resistant to variation and/or fluctuation.

3. The method of claim 1 additionally comprising the step of providing the liquid from a reservoir coupled to said bore.

4. The method of claim 3, wherein said needle and said reservoir are located within a housing and wherein said method additionally comprises the step of securing said housing on the body of the subject, whereupon said needle penetrates the skin of the subject so that the liquid may pass into said bore and out of said outlet.

5. The method of claim 4, wherein said housing additionally comprises a driving means for driving the liquid into said bore and out of said outlet.

6. The method of claim 1, wherein said needle includes a plurality of apertures, each of which is located a different distance from said sharpened end of said needle, and wherein the liquid is delivered to contiguous internal tissue from said plurality of apertures.

7. A needle for delivery of a liquid into or through the skin of a subject, said needle comprising a tubular sidewall and a sharpened end for penetrating the skin of the subject to enable said needle to be located in the skin or beneath the skin, said tubular sidewall having a longitudinal axis, a bore extending along said longitudinal axis, an exterior surface and at least one aperture in the form of a cut in said sidewall extending transversely to said longitudinal axis and in communication with said bore, said aperture having an inlet at said bore and an outlet at said exterior surface, said outlet being substantially larger than said inlet and shaped to be resistant to clogging to facilitate the delivery of the liquid to an area in the skin or beneath the skin contiguous said at least one aperture.

8. The needle of claim 7, wherein said cut is linear.

9. The needle of claim 7, wherein said at least one aperture includes an aperture wall, and wherein at least one portion of said aperture wall is oriented at an angle non-parallel to the radius of said internal bore.

10. The needle of claim 7, wherein said sharpened end of said needle is in the form of a beveled or conical tip and said cut extends in a direction at an angle to said longitudinal axis which is greater than or equal to the angle between the beveled or conical surface and said longitudinal axis.

11. The needle of claim 7, wherein said cut extends in a direction approximately perpendicular to said longitudinal axis.

12. The needle of claim 7, wherein width of said cut at said outlet is greater than the width of said cut at said inlet.

13. The needle of claim 12, wherein width of said cut at said outlet is at least twice the width of said cut at said inlet.

14. The needle of claim 7, wherein said at least one aperture includes an aperture wall, wherein said sidewall has a C-shaped cross section at the locus of said at least one aperture, and wherein portions of said aperture wall contiguous with said inlet are coplanar.

15. The needle of claim 7, wherein said needle includes a plurality of apertures, each of which is located a different distance from said sharpened end of said needle.

16. The needle of claim 7, wherein said cut has a pair of ends and wherein said depth of said cut increases from zero at either end of said cut to a maximum depth towards the center of said cut which is greater than or equal to the thickness of said sidewall at that point.

17. A needle for the delivery of a liquid to internal tissue of a subject, said needle comprising a tubular sidewall and a sharpened end for penetrating the skin of the subject to enable said needle to be located in the skin or beneath the skin, said sidewall having a longitudinal axis, a bore extending along said longitudinal axis, an exterior surface and at least one aperture in the form of a cut in said tubular sidewall extending transversely to said longitudinal axis and in communication with said central bore, said aperture having an inlet at said central bore and an outlet at said exterior surface, said outlet being substantially larger than said inlet so that the liquid passes through said at least one aperture and out of said outlet to engage a relatively large area in the skin or beneath the skin contiguous said at least one aperture to facilitate the transfer of the liquid to that area at a flow rate that is resistant to variations and/or fluctuations.

18. The needle of claim 17, wherein said cut is linear.

19. The needle of claim 17, wherein said at least one aperture includes an aperture wall, and wherein at least one portion of said aperture wall is oriented at an angle non-parallel to the radius of said internal bore.

20. The needle of claim 17, wherein said sharpened end of said needle is in the form of a beveled or conical tip and said cut extends in a direction at an angle to said longitudinal axis which is greater than or equal to the angle between the beveled or conical surface and said longitudinal axis.

21. The needle of claim 17, wherein said cut extends in a direction approximately perpendicular to said longitudinal axis.

22. The needle of claim 17, wherein width of said cut at said outlet is greater than the width of said cut at said inlet.

23. The needle of claim 22, wherein width of said cut at said outlet is at least twice the width of said cut at said inlet.

24. The needle of claim 17, wherein said at least one aperture includes an aperture wall, wherein said sidewall has a C-shaped cross section at the locus of said at least one aperture, and wherein portions of said aperture wall contiguous with said inlet are coplanar.

25. The needle of claim 17, wherein said needle includes a plurality of apertures, each of which is located a different distance from said sharpened end of said needle.

26. The needle of claim 17, wherein said cut has a pair of ends and wherein said depth of said cut increases from zero at either end of said cut to a maximum depth towards the center of said cut which is greater than or equal to the thickness of said sidewall at that point.

* * * * *